US012747255B2

(12) United States Patent
LI et al.

(10) Patent No.: US 12,747,255 B2
(45) Date of Patent: Sep. 29, 2026

(54) LOW-ODOR WATER-SOLUBLE COPPER CHLOROPHYLLIN AND PREPARATION METHOD AND USE THEREOF

(71) Applicant: HENAN ZHONGDA HENGYUAN BIOTECHNOLOGY STOCK CO., LTD., Luohe City (CN)

(72) Inventors: Honglong LI, Luohe City (CN); Xiaosong Xu, Luohe City (CN); Ziheng Jin, Luohe City (CN); Linzheng Li, Luohe City (CN); Yulian Guo, Luohe City (CN); Wenjin Zhang, Luohe City (CN); Chunfeng Yu, Luohe City (CN)

(73) Assignee: HENAN ZHONGDA HENGYUAN BIOTECHNOLOGY STOCK CO., LTD., Luohe City (CN)

( * ) Notice: Subject to any disclaimer, the term of this patent is extended or adjusted under 35 U.S.C. 154(b) by 509 days.

(21) Appl. No.: 18/377,750

(22) Filed: Oct. 6, 2023

(65) Prior Publication Data

US 2025/0115623 A1 Apr. 10, 2025

(51) Int. Cl.

| | |
|---|---|
| ***C07F 1/08*** | (2006.01) |
| ***A23L 5/47*** | (2016.01) |
| ***A23L 21/10*** | (2016.01) |
| ***A61K 8/58*** | (2006.01) |
| ***A61K 31/555*** | (2006.01) |

(52) U.S. Cl.

CPC .................. *C07F 1/08* (2013.01); *A23L 5/47* (2016.08); *A23L 21/10* (2016.08); *A61K 8/58* (2013.01); *A61K 31/555* (2013.01)

(58) Field of Classification Search

CPC ......... C07F 1/08; A61K 31/30; A61K 31/555; A61K 8/11

See application file for complete search history.

(56) References Cited

U.S. PATENT DOCUMENTS

| | | | | |
|---|---|---|---|---|
| 6,287,542 B1 * | 9/2001 | Bernard | ................... | A61K 8/11 424/49 |
| 2008/0139524 A1 * | 6/2008 | Bailey | .................. | A61K 31/555 514/185 |
| 2024/0206519 A1 * | 6/2024 | Li | ............................ | A23L 2/52 |

FOREIGN PATENT DOCUMENTS

| | | |
|---|---|---|
| CN | 1634920 A * | 7/2005 |

OTHER PUBLICATIONS

T. Tumolo et al., 46 Food Research International, 451-459 (2012) (Year: 2012).*

Y. Kim et al., 72 Journal of Cosmetic Science, pp. 460-462 (2021) (Year: 2021).*

V. Singh et al., 123 Food and Bioproducts Processing, 322-334 (2020) (Year: 2020).*

A. Mortensen, 78 Pure and Applied Chemistry, 1477-1491 (2006) (Year: 2006).*

A. Humphrey, 5 Food Science, 57-67 (1980) (Year: 1980).*

J. Shang et al., Hindawi, 1-9 (2020) (Year: 2020).*

* cited by examiner

*Primary Examiner* — Alexander R Pagano

(57) ABSTRACT

The invention relates to the technical field of natural product preparation, and specifically to low-odor water-soluble copper chlorophyllin and a preparation method and use thereof. In the invention, a copper chlorophyllin paste is used as a raw material and is subjected to deodorization treatment, colloidal solution emulsification treatment, and secondary microencapsulation and drying treatment, and saponification with a strong base such as sodium hydroxide is not used. Therefore, the process route is safer and simpler. The obtained low-odor water-soluble copper chlorophyllin has good water solubility, is not easy to precipitate in a solution with a pH of 2 to 4.0, has good stability and low odor, and is not easy to "bleed" when used in jelly and jam products.

7 Claims, 1 Drawing Sheet

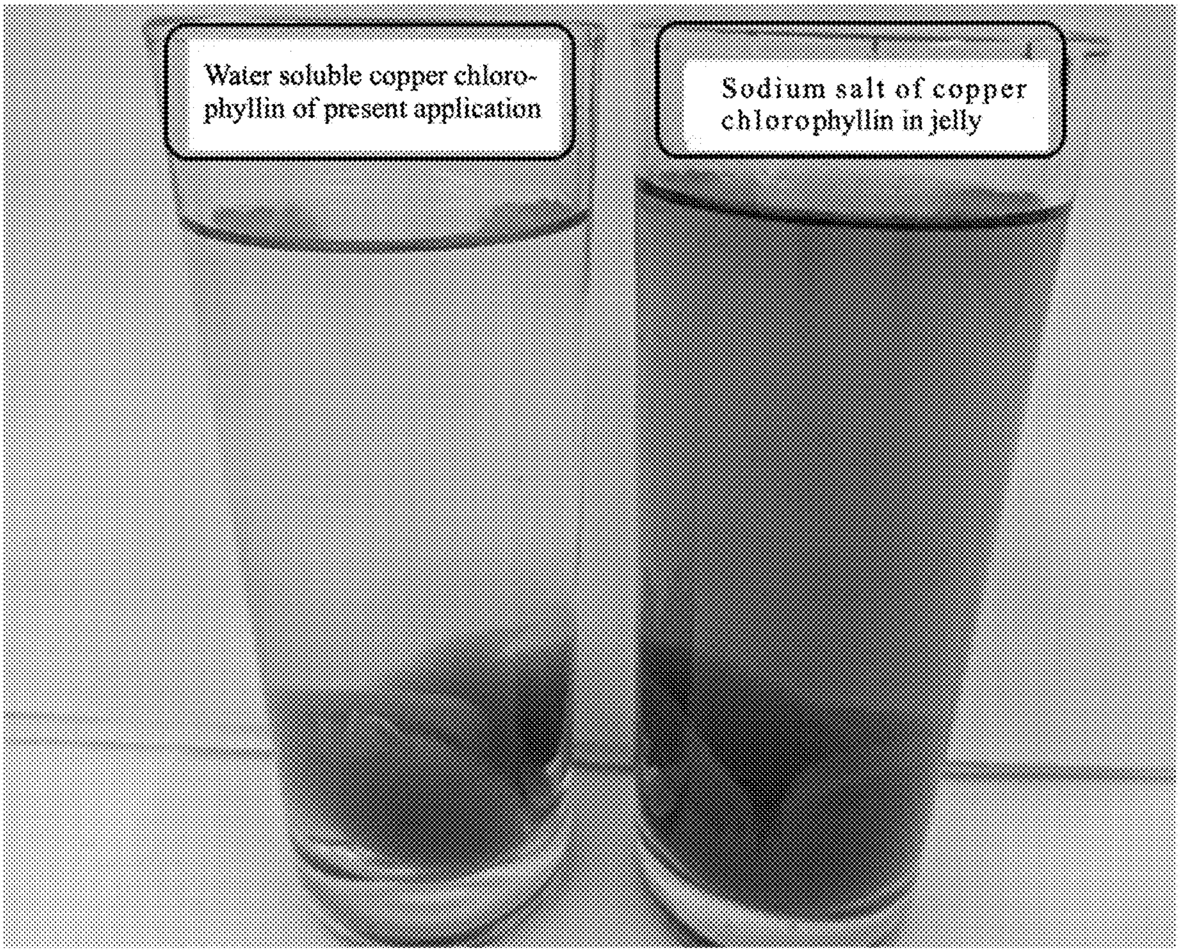
Water soluble copper chloro-
phyllin of present application
Sodium salt of copper
chlorophyllin in jelly

LOW-ODOR WATER-SOLUBLE COPPER CHLOROPHYLLIN AND PREPARATION METHOD AND USE THEREOF

FIELD OF THE INVENTION

The invention relates to the technical field of natural product preparation, and specifically to low-odor water-soluble copper chlorophyllin and a preparation method and use thereof.

DESCRIPTION OF THE RELATED ART

As a metalloporphyrin compound, copper chlorophyll has higher stability than chlorophyll. In addition, copper chlorophyll has high application value in foods, medicines, and cosmetics because of its special structure and the chelated nutrient elements in its derivatives. Copper chlorophyll and its sodium salts can be widely used as food colorants in cream, candy, baking, beverage, fruit wine, jelly, canned food and other foods, mainly for coloring or improving the natural green of food and enhancing the value of products. Studies have proved that copper chlorophyll and its sodium salts have good health effects such as eliminating inflammation and protecting liver, so they have also been used in daily chemical products such as toothpaste, facial cleanser, and shower gel. In addition, as an important raw material for the treatment of hepatitis, stomach diseases, and duodenal ulcer, copper chlorophyll and its sodium salts have also been used in the field of medicine.

At present, copper chlorophyllin and its sodium salts available on the market are mostly prepared using silkworm excrement as a raw material, and the obtained products inevitably contain proteins, fats, and their degradation products in silkworm excrement, leading to a distinct unpleasant "odor or smell", seriously affecting the application of copper chlorophyllin and its sodium salts in end products. In existing production processes, to achieve the water solubility of copper chlorophyllin, saponification with sodium hydroxide is usually adopted. The obtained product, though having good water solubility, is easy to precipitate in a solution with a pH of lower than 4.0, has poor photostability and thermal stability, and is easy to "bleed" when used in jelly and jam products. In addition, sodium hydroxide used in the process is a strong alkali, leading to safety risks in the production process. Moreover, the subsequent operations such as purification results in a long process route, high costs, and so on.

SUMMARY OF THE INVENTION

To overcome the shortcomings and disadvantages of long process route, high costs, poor photostability and thermal stability of the product, and odor in the preparation of copper chlorophyllin in the prior art, a main objective of the invention is to provide a method for preparing low-odor water-soluble copper chlorophyllin. In the method, a copper chlorophyllin paste is used as a raw material and is subjected to deodorization treatment, colloidal solution emulsification treatment, and secondary microencapsulation and drying treatment, and saponification with a strong base such as sodium hydroxide is not used. Therefore, the process route is safer and simpler.

Another objective of the invention is to provide low-odor water-soluble copper chlorophyllin prepared by the above method. The product has good water solubility, is not easy to precipitate in an acidic solution with a pH of 2.0 to 4.0, has good stability and low odor (smell), and is not easy to "bleed" when used.

Still another objective of the invention is to provide use of the low-odor water-soluble copper chlorophyllin.

The objectives of the invention are accomplished through the following technical solutions.

A method for preparing low-odor water-soluble copper chlorophyllin, including:

(1) deodorization: washing a copper chlorophyllin paste with an alcohol solution containing a phosphate or disodium ethylenediaminetetraacetate while stirring, for solid-liquid separation to obtain an alcohol solution and a precipitate;

(2) concentration: removing residual alcohols in the precipitate prepared in the step (1) by evaporation under vacuum to obtain a low-odor refined copper chlorophyllin ointment;

(3) dilution: diluting the low-odor refined copper chlorophyllin ointment prepared in the step (2) with vegetable oil to obtain a low-odor copper chlorophyllin raw material with good fluidity;

(4) emulsification and homogenization: mixing the low-odor copper chlorophyllin raw material prepared in the step (3) as a core material with a solution of a colloidal wall material, followed by vacuum high-speed emulsification and ultra-high-pressure homogenization to obtain a low-odor water-soluble copper chlorophyllin emulsion; and (5) secondary microencapsulation: carrying out spray granulation of the low-odor water-soluble copper chlorophyll emulsion prepared in the step (4), and simultaneously spraying a coating material for secondary encapsulation in the spray granulation process; and finally drying to obtain low-odor water-soluble copper chlorophyllin.

The copper chlorophyllin paste in the step (1) is prepared from silkworm excrement as a raw material, and preferably has a specific absorbance of E70 to E80.

The phosphate in the step (1) is preferably at least one of sodium hexametaphosphate, sodium polyphosphate, sodium pyrophosphate, and sodium tripolyphosphate.

The percentage by weight of the phosphate or disodium ethylenediaminetetraacetate in the alcohol solution in the step (1) is preferably 0.01% to 5%.

The percentage by weight of the phosphate or disodium ethylenediaminetetraacetate in the alcohol solution in the step (1) is more preferably 0.15% to 0.3%.

The alcohol solution in the step (1) is preferably at least one of ethanol, isopropanol, and n-butanol.

The percentage by volume of alcohol in the alcohol solution in the step (1) is preferably 75 vol % to 100 vol %, more preferably 90 vol % to 95 vol %.

Conditions of the washing in the step (1) preferably include: a stirring temperature of 30° C. to 50° C. and a stirring duration of 15 min to 90 min; and the washing is carried out for 1 to 5 times.

The washing in the step (1) specifically includes the following steps:

heating the copper chlorophyllin paste at 30° C. to 50° C. in a water bath for 30 min to 60 min in advance, and then adding the alcohol solution and stirring uniformly while holding at this temperature; and adding the phosphate or disodium ethylenediaminetetraacetate, and stirring for 15 min to 90 min while holding at this temperature.

The mass ratio of the alcohol solution to the copper chlorophyllin paste in the step (1) is preferably (2-6): 1.

The solid-liquid separation in the step (1) may be carried out through centrifugation or filtration.

The centrifugation may be implemented by one of a butterfly centrifuge, a tripod centrifuge, a horizontal screw centrifuge, and a tubular centrifuge.

The alcohol liquid obtained after the solid-liquid separation in the step (1) may be further concentrated under reduced pressure and recycled.

Conditions of the evaporation in the step (2) preferably include: a vacuum evaporation temperature of 50° C. to 90° C. and a vacuum degree of −0.08 MPa to −0.1 MPa.

The vegetable oil in the step (3) is preferably at least one of soybean salad oil, sunflower seed oil, corn oil, safflower seed oil, tea seed oil, and cottonseed oil.

The mass ratio of the vegetable oil in the step (3) to the copper chlorophyll paste in the step (1) is preferably (0.1-10): 1.

The mass ratio of the vegetable oil in the step (3) to the copper chlorophyll paste in the step (1) is more preferably (0.1-1): 1.

The colloidal wall material in the step (4) is preferably at least one of sodium octenylsuccinate starch, hydroxypropyl starch, acetate starch, carboxymethyl starch, phosphate starch, resistant dextrin, microporous starch, acacia gum, ghatti gum, xanthan gum, pullulan, fucoidan, trehalose, and lactose.

The percentage by weight of the colloidal wall material in the colloidal wall material solution in the step (4) is 5% to 75%.

The colloidal wall material solution in the step (4) preferably further includes at least one of a filler and a natural antioxidant.

The filler is at least one of maltodextrin, microcrystalline cellulose, corn syrup, white sugar, lactitol, erythritol, maltitol, sorbitol, α-cyclodextrin, β-cyclodextrin, and γ-cyclodextrin.

The percentage by weight of the filler in the colloidal wall material solution is 5% to 75%.

The natural antioxidant is at least one of ascorbic acid, sodium erythorbate, tea polyphenols, quercetin, enzymatically modified isoquercitrin, rutin, epigallocatechin gallate (EGCG), and vitamin E (VE).

The percentage by weight of the natural antioxidant in the colloidal wall material solution is 0.01% to 1%.

The mass ratio of solute in the colloidal wall material solution to the core material in the step (4) is preferably (1:1) to (1:0.1).

Conditions of the vacuum high-speed emulsification in the step (4) preferably include: a pressure of −0.05 MPa to −0.1 MPa and a temperature of 10° C. to 70° C., where the temperature is more preferably 25° C. to 50° C.

The pressure of the ultra-high-pressure homogenization in the step (4) is preferably 60 MPa to 200 MPa, more preferably 70 MPa to 180 MPa.

The coating material in the step (5) is preferably at least one of starch and maltodextrin.

The DE value of the maltodextrin is preferably 5 to 20.

The coating material in the step (5) is 10% to 30% of the mass of the final product.

Conditions of the spray granulation in the step (5) preferably include: an air inlet temperature of 160° C. to 200° C., an air outlet temperature of 70° C. to 100° C., and a bottom air temperature of 70° C. to 90° C.

Also disclosed is low-odor water-soluble copper chlorophyllin prepared by the above method.

Also disclosed is use of the low-odor water-soluble copper chlorophyllin in foods, cosmetics, and medicines.

The principle of the invention is as follows:

In the invention, odorous components (mainly some small molecules, such as degradation products of fatty acids and degradation products of proteins) in the copper chlorophyll paste are dissolved in alcohol such as ethanol and isopropanol, and the phosphate or disodium ethylenediaminetetraacetate are used as chelating agents to fix copper chlorophyll, to reduce the process loss in the process of deodorization. Then, copper chlorophyllin was prepared into a nanoemulsion by processes such as emulsification and homogenization with colloidal such as acacia gum and modified starch as the wall material. Finally, the nanoemulsion is encapsulated by starch, maltodextrin, or the like in the spray granulation process to obtain a low-odor water-soluble copper chlorophyllin microcapsule product with good water solubility.

Compared with the prior art, the present invention has the following beneficial effects:

(1) In the invention, the copper chlorophyll paste as a raw material is purified through "deodorization", emulsified and homogenized using a colloidal solution, and then subjected to secondary encapsulation using maltodextrin, starch, or the like as the coating material. In the invention, saponification with a strong base such as sodium hydroxide is not used, so the process route is safer and simpler.

(2) By using the alcohol solution containing the phosphate or disodium ethylenediaminetetraacetate for refining, the invention can effectively remove small molecular degradation products such as degradation products of fatty acids and degradation products of proteins in the copper chlorophyll raw material, and significantly reduce the unpleasant odor and smell in the final product, thereby significantly improving the effect of use of copper chlorophyll in the final product.

(3) In the invention, after copper chlorophyll is emulsified using the colloidal solution and subjected to secondary encapsulation and drying using the coating material such as maltodextrin and starch, the obtained product has good water solubility, can significantly improve the photostability and thermal stability of the product, has good stability in an acidic solution with a pH of 2.0 to 4.0, and is not easy to precipitate.

(4) The low-odor water-soluble copper chlorophyll product prepared by the invention has much higher stability when applied in jelly and jam products than the products of the prior art, and is not easy to "bleed".

BRIEF DESCRIPTION OF THE DRAWINGS

FIG. 1 is an image showing bleeding effects of low-odor water-soluble copper chlorophyllin produced in Example 1 and a commercially available sodium salt of copper chlorophyllin when used in jelly.

DETAILED DESCRIPTION OF THE PREFERRED EMBODIMENTS

The invention will be further described in detail below with reference to examples and the accompanying drawings, but the implementation of the invention is not limited thereto.

The raw material copper chlorophyll paste in the examples was commercially available, and the copper chlorophyll paste was prepared from silkworm excrement as a raw material.

Example 1

(1) Deodorization: 2000 g of a copper chlorophyll paste with a specific absorbance of E70 was weighed, and added into a reactor with a stirrer. Warm water at a temperature of 45° C. to 50° C. was introduced into the interlayer of the reactor and circulated to heat the copper chlorophyll paste for 45 min. When the material presented a good fluidity, 8000 g of 95 vol % ethanol was added and stirred uniformly. Then, 200 g of a 10 wt % sodium hexametaphosphate solution was added slowly, held at the temperature, and stirred for 40 min. The supernatant was separated from the precipitate using a settling tripod centrifuge (centrifuged at 1500 rpm for 25 min) to finish the first washing. The collected precipitate was added into the reactor. Another 8000 g of 95 vol % ethanol was added and stirred uniformly. Then, 200 g of the 10 wt % sodium hexametaphosphate solution was added slowly, held at the temperature, and stirred for 40 min. The supernatant was separated from the precipitate using a settling tripod centrifuge (centrifuged at 1500 rpm for 20 min) again to finish the second cleaning. The cleaning was repeated for 4 times according to the above operations.

(2) Concentration: The supernatant (ethanol) collected in the step (1) was concentrated under reduced pressure, stored separately, and recycled. The precipitate was collected, and evaporated at a temperature of 80±5° C. and a vacuum degree of −0.09 MPa to remove the residual ethanol until the residual amount of ethanol was less than or equal to 200 ppm, to obtain 1250 g of a low-odor refined copper chlorophyllin ointment with a specific absorbance of E126.2.

(3) Dilution: 750 g of non-transgenic soybean salad oil was weighed, heated to 70° C. to 75° C., added into the low-odor refined copper chlorophyllin ointment prepared in the step (2), and stirred uniformly, to obtain 2000 g of a low-odor copper chlorophyllin raw material with good fluidity and a specific absorbance of E71.

(4) Emulsification and homogenization: 110 g of acacia gum, 25 g of hydroxypropyl starch, 40 g of maltodextrin (DE18), 23 g of white sugar, and 2 g of tea polyphenols were weighed and dissolved in 200 g of deionized water to prepare a water-soluble colloidal wall material solution containing a colloidal wall material in an amount of 33.75 wt %. 200 g of the low-odor copper chlorophyllin raw material prepared in the step (3) was weighed and mixed with the water-soluble colloidal wall material solution, and subjected to vacuum high-speed emulsification at a pressure of −0.08 MPa and a temperature of 45° C. to 50° C. for 25 min, until the emulsified solution was uniformly dispersed. The emulsified solution was homogenized twice by ultra-high-pressure homogenization at a pressure of 135 MPa to obtain a stable low-odor water-soluble copper chlorophyllin emulsion, and the measured particle size D50 was less than or equal to 500 nm.

(5) Secondary microencapsulation: Spray granulation of the low-odor water-soluble copper chlorophyll emulsion prepared in the step (4) was carried out, and simultaneously starch was sprayed for secondary encapsulation in the spray granulation process. Conditions of the spray granulation included: an air inlet temperature of 160° C. to 190° C., an air outlet temperature of 70° C. to 90° C., and a bottom air temperature of 70° C. to 85° C. in drying. The amount of the starch used was 24% of the mass of the final product, to obtain low-odor water-soluble copper chlorophyllin.

Example 2

(1) Deodorization: 2500 g of a copper chlorophyll paste with a specific absorbance of E82 was weighed, and added into a reactor with a stirrer. Warm water at a temperature of 45° C. to 50° C. was introduced into the interlayer of the reactor and circulated to heat the copper chlorophyll paste for 60 min. When the material presented a good fluidity, 8700 g of 95 vol % ethanol was added and stirred uniformly. Then, 230 g of a 10 wt % disodium ethylenediaminetetraacetate solution was added slowly, held at the temperature, and stirred for 50 min. The supernatant was separated from the precipitate using a settling tripod centrifuge (centrifuged at 1500 rpm for 25 min) to finish the first washing. The collected precipitate was added into the reactor. Another 8700 g of 95 vol % ethanol was added and stirred uniformly. Then, 230 g of the 10 wt % disodium ethylenediaminetetraacetate solution was added slowly, held at the temperature, and stirred for 40 min. The supernatant was separated from the precipitate using a settling tripod centrifuge (centrifuged at 1500 rpm for 20 min) again to finish the second cleaning. The cleaning was repeated for 3 times according to the above operations.

(2) Concentration: The supernatant (ethanol) collected in the step (1) was concentrated under reduced pressure, stored separately, and recycled. The precipitate was collected, and evaporated at a temperature of 80±5° C. and a vacuum degree of −0.09 MPa to remove the residual ethanol until the residual amount of ethanol was less than or equal to 200 ppm, to obtain 1370 g of a low-odor refined copper chlorophyllin ointment with a specific absorbance of E152.6.

(3) Dilution: 1000 g of sunflower seed oil was weighed, heated to 75° C. to 80° C., added into the low-odor refined copper chlorophyllin ointment prepared in the step (2), and stirred uniformly, to obtain 2370 g of a low-odor copper chlorophyllin raw material with good fluidity and a specific absorbance of E86.

(4) Emulsification and homogenization: 135 g of hydroxypropyl starch, 5 g of pullulan, 70 g of maltodextrin (DE20), 25 g of white sugar, and 2 g of tea polyphenols were weighed and dissolved in 200 g of deionized water to prepare a water-soluble colloidal wall material solution containing a wall material in an amount of 32.03 wt %. 200 g of the low-odor copper chlorophyllin raw material prepared in the step (3) was weighed and mixed with the water-soluble colloidal wall material solution, and subjected to vacuum high-speed emulsification at a pressure of −0.08 MPa and a temperature of 45° C. to 50° C. for 35 min, until the emulsified solution was uniformly dispersed. The emulsified solution was homogenized twice by ultra-high-pressure homogenization at a pressure of 145 MPa to obtain a stable low-odor water-soluble copper chlorophyllin emulsion, and the measured particle size D50 was less than or equal to 500 nm.

(5) Secondary microencapsulation: Spray granulation of the low-odor water-soluble copper chlorophyll emulsion prepared in the step (4) was carried out, and simultaneously starch was sprayed for secondary encapsulation in the spray granulation process. Conditions of the spray granulation included: an air inlet temperature of 160° C. to 190° C., an air outlet temperature of 70° C. to 90° C., and a bottom air temperature of 70° C. to 85° C. in drying. The amount of the starch used was 20% of the mass of the final product, to obtain low-odor water-soluble copper chlorophyllin.

Example 3

(1) Deodorization: 1500 g of a copper chlorophyll paste with a specific absorbance of E78 was weighed, and added into a reactor with a stirrer. Warm water at a temperature of 35° C. to 40° C. was introduced into the interlayer of the reactor and circulated to heat the copper chlorophyll paste for 45 min. When the material presented a good fluidity, 6000 g of n-butanol was added and stirred uniformly. Then, 170 g of a 7 wt % sodium pyrophosphate solution was added slowly, held at the temperature, and stirred for 25 min. The supernatant was separated from the precipitate using a tubular centrifuge (centrifuged at 13000 rpm for 15 min) to finish the first washing. The collected precipitate was added into the reactor. Another 6000 g of n-butanol was added and stirred uniformly. Then, 170 g of the 7 wt % sodium pyrophosphate solution was added slowly, held at the temperature, and stirred for 25 min. The supernatant was separated from the precipitate using a tubular centrifuge (centrifuged at 13000 rpm for 15 min) again to finish the second cleaning. The cleaning was repeated for 3 times according to the above operations.

(2) Concentration: The supernatant (n-butanol) collected in the step (1) was concentrated under reduced pressure, stored separately, and recycled. The precipitate was collected, and evaporated at a temperature of 87.5±2.5° C. and a vacuum degree of −0.09 MPa to remove the residual n-butanol until the residual amount of n-butanol was less than or equal to 300 ppm, to obtain 876 g of a low-odor refined copper chlorophyllin ointment with a specific absorbance of E136.1.

(3) Dilution: 624 g of corn oil was weighed, heated to 65° C. to 70° C., added into the low-odor refined copper chlorophyllin ointment prepared in the step (2), and stirred uniformly, to obtain 1500 g of a low-odor copper chlorophyllin raw material with good fluidity and a specific absorbance of E78.8.

(4) Emulsification and homogenization: 15 g of ghatti gum, 100 g of acacia gum, 20 g of γ-cyclodextrin, 40 g of maltodextrin (DE10), 25 g of trehalose, and 2 g of EGCG were weighed and dissolved in 220 g of deionized water to prepare a water-soluble colloidal wall material solution containing a colloidal wall material in an amount of 33.18 wt %. 200 g of the low-odor copper chlorophyllin raw material prepared in the step (3) was weighed and mixed with the water-soluble colloidal wall material solution, and subjected to vacuum high-speed emulsification at a pressure of −0.08 MPa and a temperature of 45° C. to 50° C. for 40 min, until the emulsified solution was uniformly dispersed. The emulsified solution was homogenized twice by ultra-high-pressure homogenization at a pressure of 130 MPa to obtain a stable low-odor water-soluble copper chlorophyllin emulsion, and the measured particle size D50 was less than or equal to 500 nm.

(5) Secondary microencapsulation: Spray granulation of the low-odor water-soluble copper chlorophyll emulsion prepared in the step (4) was carried out, and simultaneously maltodextrin was sprayed for secondary encapsulation in the spray granulation process. Conditions of the spray granulation included: an air inlet temperature of 160° C. to 190° C., an air outlet temperature of 70° C. to 90° C., and a bottom air temperature of 70° C. to 85° C. in drying. The amount of the maltodextrin used was 20% of the mass of the final product, to obtain low-odor water-soluble copper chlorophyllin.

Comparative Example 1

This comparative example is different from Example 1 in that sodium hexametaphosphate was not added.

Comparative Example 2

This comparative example is different from Example 2 in that disodium ethylenediaminetetraacetate was not added.

Comparative Example 3

This comparative example is different from Example 3 in that sodium pyrophosphate was not added.

EFFECT EXAMPLES (1) Specific Absorbance Detection (a) 0.1 g (accurate to 0.0001 g) of a sample to be tested was accurately weighed and placed in a clean small beaker of 50 mL. Distilled water was added, and carefully stirred with a glass rod, until the sample was completely dissolved. The solution was slowly transferred into a 100 mL volumetric flask under guidance of the glass rod (before transferring, the volumetric flask was rinsed with distilled water). The beaker was repeatedly rinsed with a small amount of distilled water until it was clean. The wash solution was also injected into the volumetric flask, then distilled water was added to make up the volume to the mark and shaken until uniform.

(b) 1 mL of the diluent was accurately taken using a 1 mL pipette and placed in a 100 mL volumetric flask (the pipette was first rinsed repeatedly with the above diluent for at least 3 times, and the volumetric flask was rinsed clean with a phosphate buffer solution pH 7.5). The phosphate buffer solution pH 7.5 was added to make up the volume to the mark and shaken until uniform, to obtain a test solution. The phosphate buffer solution pH 7.5 was prepared by: mixing 21 parts of 0.15 M disodium hydrogen phosphate (GB 1263-77 analytically pure) and 4 parts of 0.15 M potassium dihydrogen phosphate (GB 1274-77 analytically pure).

(c) The phosphate buffer solution pH 7.5 was used as a reference solution. The test solution was filled into a 1 cm cuvette, and the absorbance A of the test solution was measured at 405 nm using a spectrophotometer.

(d) Specific absorbance calculation:

$$E_{405nm} = \frac{A}{m} \times 100$$

where E: specific absorbance; A: absorbance at 405 nm; m: sample weight, g; 100: dilution factor.

(2) Particle Size Measurement (a) A proper amount of the sample was tested with a sampling spoon and added into a measuring cup.

(b) A proper amount of a dispersant was added dropwise into the measuring cup and the suspension was stirred with a glass rod. After the sample was well mixed with the liquid, water was added, usually to the mark of 50 mL.

(c) The measuring cup was put into an ultrasonic cleaner. The liquid level in the cleaning tank was about ½ of the total height of the measuring cup. The ultrasonic cleaner was powered on to vibrate for about 2 min (the vibration time may be changed depending on the specific sample, and for samples that are easy to sink, the liquid in the cup should be stirred with a glass rod while vibrating).

(d) Measurement. The sample test operation was completed according to steps instructed by a laser particle size analyzer (TopSizer from Zhuhai OMEC Instruments Co., Ltd.).

TABLE 1

Specific absorbance and particle size of low-odor water-soluble copper chlorophyll prepared in Examples 1 to 3

| Examples | Specific absorbance | Particle size (D50) |
|---|---|---|
| Example 1 | E30.2 | 482 nm |
| Example 2 | E35.3 | 368 nm |
| Example 3 | E35.6 | 428 nm |

(3) Test of Precipitation Effects in pH 3.0 Solution

The low-odor water-soluble copper chlorophyllin prepared in Examples 1 to 3 were respectively formulated into 0.2 wt % solutions having a pH of 3.0. The solutions were placed at normal temperature. It was observed whether precipitation occurred in the solutions.

Results show that: after the acidic solutions formulated using the low-odor water-soluble copper chlorophyllin prepared in Examples 1 to 3 were placed at room temperature for 4 days, no precipitation was observed.

(4) Sodium salts of copper chlorophyllin (GB 26406-2011) available on the market produced by different manufacturers using conventional technologies were used as comparative examples. Comparison was made in terms of water solubility, odor, precipitation effect in pH 3.0 solution, and "bleeding" status when used in jelly. The quality of products of different technologies was observed.

(1) Water solubility: The low-odor water-soluble copper chlorophyllin prepared in Examples 1 to 3 and commercially available sodium salts of copper chlorophyllin (control 1 and control 2) were respectively formulated into a 1 wt % solution to observe their water solubility.

(2) The odors of low-odor water-soluble copper chlorophyllin prepared in Examples 1 to 3 and commercially available sodium salts of copper chlorophyllin (control 1 and control 2) were evaluated respectively.

(3) Precipitation effect in pH 3.0 solution: The method described in the above (3) was used.

(4) "Bleeding" status when used in jelly:

(a) White sugar, citric acid, jelly powder, and water were mixed in proportion, heated with low heat, stirred while heating, and boiled slowly to obtain a viscous mixture. A pigment dissolved in advance was added (while stirring). The mixture was stirred until uniform. The heating was stopped. The uniform mixture was poured into a mold and cooled to obtain jelly. The jelly contained the following components, in percentage or permillage by weight: 15% of white sugar, 0.18% of citric acid, 0.55% of jelly powder, 84.27% of water, and 0.5% % of the pigment (where the sodium salts of copper chlorophyllin in the comparative examples and the low-odor water-soluble copper chlorophyllin prepared in Examples 1 to 3 were converted into the same pigment content).

(b) Carbonated water (containing the following components, in percentage or permillage by weight: 10% of white sugar, 1.3% % of citric acid, and 0.35% % of sodium citrate) was formulated, boiled for 2 min, and cooled to room temperature to obtain a sugar-acid solution.

(c) The jelly formed in the step (a) and the sugar-acid solution prepared in the step (b) were mixed according to a mass ratio of 1:1, shaken until uniform, sealed and allowed to stand at room temperature. Color changes of the solution in the upper layer were observed and recorded.

The results are shown in Table 2. Compared with controls 1 and 2, the low-odor water-soluble copper chlorophyllin prepared in Examples 1 to 3 had good water solubility and no odor or smell, and after the acidic solutions formulated using the low-odor water-soluble copper chlorophyllin prepared in Examples 1 to 3 were placed at room temperature for 4 days, no precipitation was observed. Control 1 and control 2 had good water solubility, but a distinct odor or smell, and after the acidic solutions formulated using control 1 and control 2 were placed at room temperature for 4 days, obvious precipitation was observed.

In addition, the low-odor water-soluble copper chlorophyllin prepared in Examples 1 to 3 had high stability when used in jelly products and was not easy to "bleed", while control 1 and control 2 had an obvious "bleeding" phenomenon when used in jelly products. FIG. 1 is an image showing the use of Example 1 and Control 1 in jelly products. In Example 1, no "bleeding" occurred, while Control 1 had an obvious "bleeding" phenomenon.

TABLE 2

Comparison of quality of low-odor water-soluble copper chlorophyllin prepared in Examples 1 to 3 and commercially available sodium salts of copper chlorophyllin

| | Water solubility | Odor of solution | Precipitation effect in pH 3.0 solution (4 days) | "Bleeding" |
|---|---|---|---|---|
| Example 1 | +++++ | / | / | / |
| Example 2 | +++++ | / | / | / |
| Example 3 | +++++ | / | / | / |
| Control 1 (commercially available) | +++++ | ++++ | ++++ | ++++ |
| Control 2 (commercially available) | +++++ | +++ | +++ | +++ |

Note:
"+" indicates the quality and effect, and a larger number of "+" indicates "higher water solubility", "more distinct odor", "larger amount of precipitate", and a "more obvious bleeding effect".

(5) The specific absorbance of the low-odor refined copper chlorophyllin ointment prepared in step (2) in each of Examples 1 to 3 and Comparative Examples 1 to 3 was measured respectively, and the odor of the low-odor refined copper chlorophyllin ointment was evaluated.

The results are shown in Table 3. The refined materials prepared in Examples 1 to 3 had higher specific absorbance, showing that copper chlorophyll can be effectively fixed by using the phosphate or disodium ethylenediaminetetraacetate as the chelating agent, and small molecular degradation products such as degradation products of fatty acids and degradation products of proteins in the copper chlorophyll raw material can be effectively removed, to reduce the process loss in the process of deodorization and reduce the unpleasant odor and smell in the final product.

TABLE 3

Evaluation of specific absorbance and odor of refined materials prepared in Examples 1 to 3 and Comparative Examples 1 to 3

| Examples | Specific absorbance of refined material | "Odor" of refined material |
|---|---|---|
| Example 1 | 126.2 | / |
| Example 2 | 152.6 | / |
| Example 3 | 136.1 | / |
| Comparative Example 1 | 89.1 | + |
| Comparative Example 2 | 92.5 | + |
| Comparative Example 3 | 86.6 | + |

The above examples are preferred embodiments of the present invention, but the embodiments of the present invention are not limited to thereto. Any other changes, modifications, replacements, combinations, and simplifications may be made without departing from the spirit and scope of the present invention, which are all embraced in the scope of the present invention.

What is claimed is:

1. A method for preparing a low-odor water-soluble copper chlorophyllin, comprising:

(1) deodorization: washing a copper chlorophyllin paste with an alcohol solution containing a phosphate or disodium ethylenediaminetetraacetate while stirring, conducting a solid-liquid separation to obtain an alcohol solution and a precipitate;

(2) concentration: removing residual alcohols in the precipitate prepared in the step (1) by evaporation under vacuum to obtain a low-odor refined copper chlorophyllin ointment;

(3) dilution: diluting the low-odor refined copper chlorophyllin ointment prepared in the step (2) with vegetable oil to obtain a low-odor copper chlorophyllin raw material with good fluidity;

(4) emulsification and homogenization: mixing the low-odor copper chlorophyllin raw material prepared in the step (3) as a core material with a solution of a colloidal wall material, followed by vacuum high-speed emulsification and ultra-high-pressure homogenization to obtain a low-odor water-soluble copper chlorophyllin emulsion; and (5) secondary microencapsulation: carrying out spray granulation of the low-odor water-soluble copper chlorophyll emulsion prepared in the step (4), and simultaneously spraying a coating material for secondary encapsulation in the spray granulation process; and finally drying to obtain the low-odor water-soluble copper chlorophyllin, wherein the colloidal material in the step (4) is at least one selected from the group consisting of sodium octenylsuccinate starch, hydroxypropyl starch, acetate starch, carboxymethyl starch, phosphate starch, resistant dextrin, microporous starch, acacia gum, ghatti gum, xanthan gum, pullulan, fucoidan, trehalose, and lactose.

2. The method for preparing the low-odor water-soluble copper chlorophyllin according to claim 1, wherein the phosphate in the step (1) is at least one selected from the group consisting of sodium hexametaphosphate, sodium polyphosphate, sodium pyrophosphate, and sodium tripolyphosphate.

3. The method for preparing the low-odor water-soluble copper chlorophyllin according to claim 1, wherein a percentage by weight of the phosphate or disodium ethylenediaminetetraacetate in the alcohol solution in the step (1) is 0.01% to 5%.

4. The method for preparing the low-odor water-soluble copper chlorophyllin according to claim 1, wherein the alcohol solution in the step (1) is at least one of ethanol, isopropanol, and n-butanol.

5. The method for preparing the low-odor water-soluble copper chlorophyllin according to claim 1, wherein conditions of the washing in the step (1) comprise: a stirring temperature of 30° C. to 50° C. and a stirring duration of 15 min to 90 min; and the washing is carried out for 1 to 5 times.

6. The method for preparing the low-odor water-soluble copper chlorophyllin according to claim 1, wherein a mass ratio of the alcohol solution to the copper chlorophyllin paste in the step (1) is (2-6):1.

7. The method for preparing the low-odor water-soluble copper chlorophyllin according to claim 1, wherein the coating material in the step (5) is at least one selected from the group consisting of starch and maltodextrin.

* * * * *